(12) United States Patent
Takeshima

(10) Patent No.: US 8,472,740 B2
(45) Date of Patent: Jun. 25, 2013

(54) APPARATUS AND METHOD FOR PROCESSING DATA

(75) Inventor: Hidenori Takeshima, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 54 days.

(21) Appl. No.: 13/232,240

(22) Filed: Sep. 14, 2011

(65) Prior Publication Data

US 2012/0183214 A1 Jul. 19, 2012

(30) Foreign Application Priority Data

Jan. 14, 2011 (JP) ................................ 2011-006373

(51) Int. Cl.
*H04N 7/26106* (2006.01)

(52) U.S. Cl.
USPC ............................ 382/244; 382/232; 382/235

(58) Field of Classification Search
USPC ................. 382/239, 232, 234, 167, 176, 238,
382/244, 235, 236; 375/240.03, E7.14, E7.211,
375/E7.048, E7.065, E7.103, E7.144; 703/2,
703/5; 358/1.15
See application file for complete search history.

(56) References Cited

U.S. PATENT DOCUMENTS 5,832,126 A * 11/1998 Tanaka .......................... 382/239
6,650,773 B1 * 11/2003 Maurer et al. ................. 382/166

FOREIGN PATENT DOCUMENTS

| JP | 8-308836 | | 11/1996 |
| JP | 2010028649 | * | 2/2010 |

OTHER PUBLICATIONS

U.S. Appl. No. 13/372,657, filed Feb. 14, 2010, Takeshima.

* cited by examiner

*Primary Examiner* — Anh Do
(74) *Attorney, Agent, or Firm* — Oblon, Spivak, McClelland, Maier & Neustadt, L.L.P.

(57) ABSTRACT

According to one embodiment, an apparatus for processing data includes a data input unit, a lossy processing unit, a buffer, a region indication unit, a lossless processing unit, and a data output unit. The data input unit is configured to input time series data. The lossy processing unit is configured to obtain first compressed data by applying lossy processing to the time series data. The buffer is configured to store the first compressed data. The region indication unit is configured to indicate at least one part of the first compressed data. The lossless processing unit is configured to obtain second compressed data by applying lossless processing to the at least one part of the first compressed data. The data output unit is configured to output the second compressed data.

8 Claims, 3 Drawing Sheets

APPARATUS AND METHOD FOR PROCESSING DATA

CROSS-REFERENCE TO RELATED APPLICATION

This application is based upon and claims the benefit of priority from Japanese Patent Application No. 2011-006373, filed on Jan. 14, 2011; the entire contents of which are incorporated herein by reference.

FIELD

Embodiments described herein relate generally to an apparatus and a method for processing data.

BACKGROUND

An ultrasonic diagnosis device sends an ultrasonic signal to an inspection target, and visualizes an internal status of the inspection target based on reflected wave information thereof. This device is used for nondestructive inspection in a medical treatment region or an industrial region.

As to the ultrasonic diagnosis device, first, by processing a signal received via a probe, two data (identical phase component data (I data) and orthogonal phase component data (Q data)) are calculated. Then, based on I data and Q data (Hereinafter, they are called "IQ data"), internal data (A-mode data, B-mode data, color Doppler data (including a direction, an averaged flow velocity, a power, a distribution), M-mode data) are calculated. By applying a coloring or a scan transform to the internal data, the inspection target is visualized as image data. Moreover, in a diagnosis using this device, the power Doppler method for visualizing power data is also used. Hereinafter, for convenience' sake, the color Doppler data and the power Doppler data are called "color Doppler data".

Regularly, the ultrasonic diagnosis device prepares a plurality of methods for visualizing IQ data and internal data as image data. A user can select any from the plurality of methods. Furthermore, some ultrasonic diagnosis device prepares a function to preserve the image data visualized. As a result, after the diagnosis in real time, the user can confirm the image data visualized in off-line. In order to switch the plurality of methods in off-line, by preserving not the image data already visualized but the reflected wave information (IQ data, or internal data) not visualized yet, the visualization processing needs to be applied to the preserved data again.

However, a data quantity of the reflected wave information is much larger than that of the image data visualized. Accordingly, preservation of all reflected wave information unprocessed is not realistic. Furthermore, if compression processing is applied to all reflected wave information inputted, processing quantity is enormous. As a result, processing time thereof becomes very long.

DETAILED DESCRIPTION

According to one embodiment, an apparatus for processing data includes a data input unit, a lossy processing unit, a buffer, a region indication unit, a lossless processing unit, and a data output unit. The data input unit is configured to input time series data. The lossy processing unit is configured to obtain first compressed data by applying lossy processing to the time series data. The buffer is configured to store the first compressed data. The region indication unit is configured to indicate at least one part of the first compressed data. The lossless processing unit is configured to obtain second compressed data by applying lossless processing to the at least one part of the first compressed data. The data output unit is configured to output the second compressed data.

Various embodiments will be described hereinafter with reference to the accompanying drawings.

One Embodiment

Figure 1:
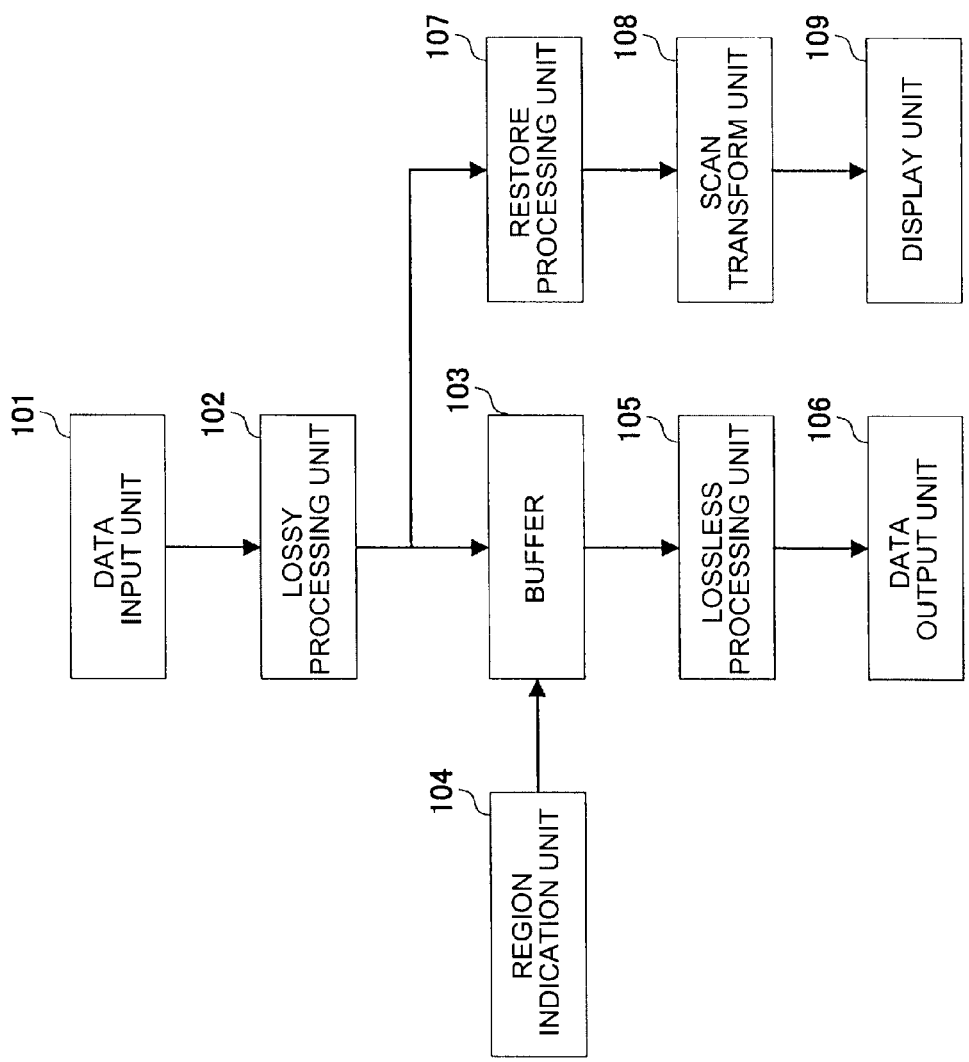
FIG. 1 is a block diagram of a data processing apparatus according to one embodiment.

FIG. 1 is a block diagram of a data processing apparatus according to one embodiment. The data processing apparatus is imagined to be executed as a part of the ultrasonic diagnosis device. By applying compression processing (For example, JPEG format, MPEG-2 format, H.264 format) to reflected wave information (IQ data, internal data), compressed data is output to an external storage. In this case, the compression processing is composed by two steps, i.e., lossy processing and lossless processing. First, the data processing apparatus executes lossy processing of the reflected wave information in real time, and stores first compressed data (applied with the lossy processing) into a buffer. Furthermore, the data processing apparatus applies restore processing (of the lossy processing) and geometric transform (for visualization) to the first compressed data, and presents image data of an inspection target to a user in real time. When the user decides this image is to be preserved by watching, the user indicates a region of a preservation target (Hereinafter, it is called "a preserve region") to the data processing apparatus. The data processing apparatus executes lossless processing to the first compressed data indicated as the preserve region, and outputs second compressed data (obtained by the lossless processing) to the external storage.

(Whole Component)

As shown in FIG. 1, the data processing apparatus of the present embodiment includes a data input unit 101, a lossy processing unit 102, a buffer 103, a region indication unit 104, a lossless processing unit 105, a data output unit 106, a restore processing unit 107, a scan transform unit 108, and a display unit 109.

The data input unit 101 inputs (two-dimensional or three-dimensional) time series data. The lossy processing unit 102 obtains first compressed data by applying lossy processing to the time series data (input to the data input unit 101). The buffer 103 stores the first compressed data (obtained by the lossy processing unit 102). The region indication unit 104 indicates a part or all of the first compressed data (stored in the buffer 103) as a preserve region. The lossless processing unit 105 obtains second compressed data by applying lossless processing to the first compressed data of the preserve region (indicated by the region indication unit 104). The data output unit 106 outputs the second compressed data (obtained by the lossless processing unit 105). The restore processing unit 107 obtains restored data by applying restore processing (of the lossy processing) to the first compressed data (obtained by the lossy processing unit 102). The scan transform unit 108 obtains a scan transformed image by applying a scan transform to the restored data (obtained by the restore processing unit 107). The display unit 109 displays the scan transformed image (obtained by the scan transform unit 108).

(Hardware Component)

Figure 2:
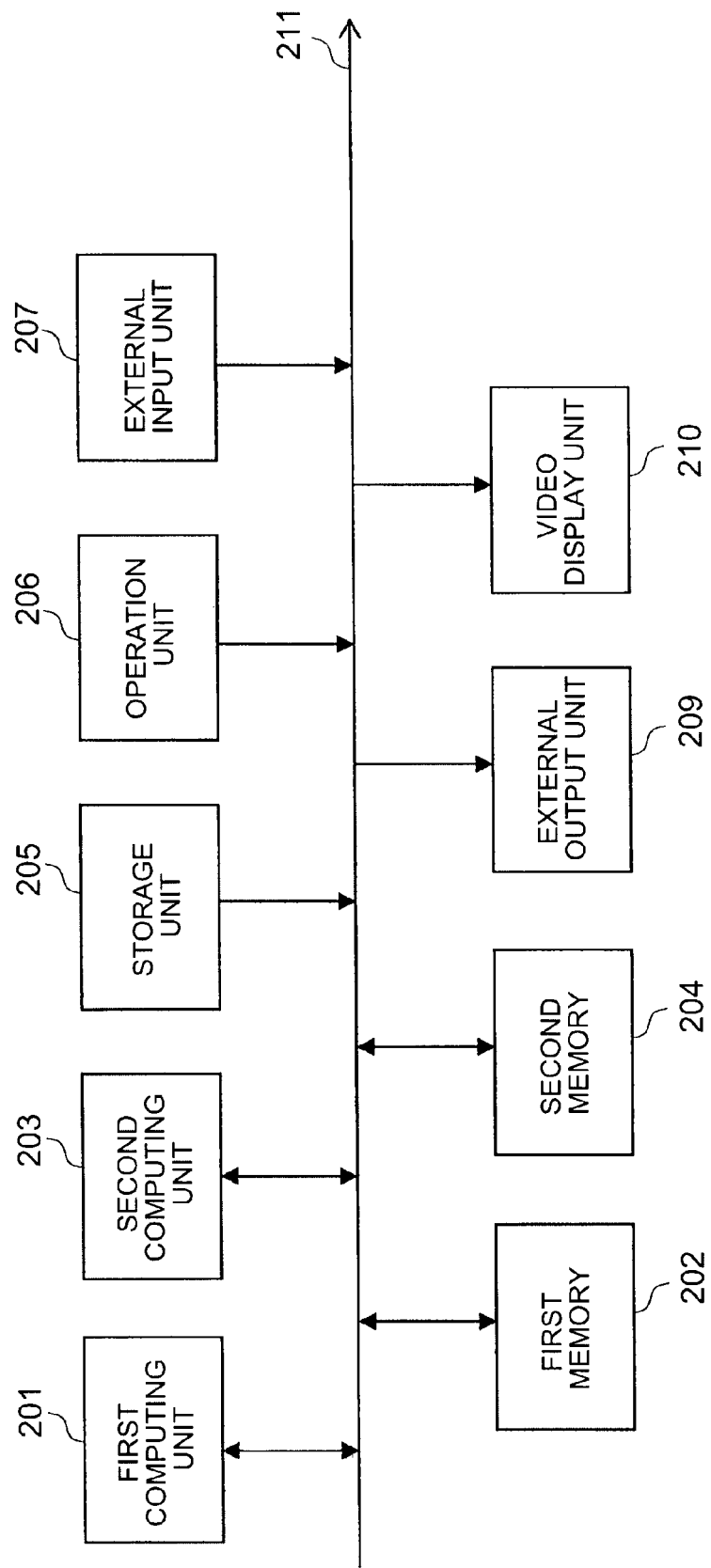
FIG. 2 is a hardware component of the data processing apparatus.

As shown in FIG. 2, the data processing apparatus of the present embodiment is composed by a hardware using a regular computer. The hardware includes a first computing unit 201, a first memory 202, a second computing unit 203, a second memory 204, a storage unit 205, an operation unit 206, an external input unit 207, an external output unit 209, a video display unit 210, and a bus 211.

The first computing unit 201 is, for example, a CPU (Central Processing Unit) to control all the apparatus. The first memory 202 is, for example, a RAM (Random Access Memory) to be quickly accessed by the first computing unit 201. The second computing unit 203 is, for example, a DSP (Digital Signal Processor) or a GPU (Graphic Processing Unit). The second memory 204 is, for example, a RAM to be quickly accessed by the second computing unit 203. The storage unit 205 is, for example, a ROM (Read Only Memory) to store various data and various programs. The operation unit 206 is, for example, a keyboard or a mouse to accept an indication input from the user. The external input unit 207 inputs a signal from an external device such as a probe. The external output unit 209 outputs data to an external storage such as a HDD (Hard Disk Drive). The video display unit 210 is, for example, a display to present a video. The bus 211 connects above-mentioned units. In the present embodiment, the second computing unit 203 has a function able to compute in parallel at the maximum "M-parallel" (M: natural number larger than or equal to two).

(Explanation of Function of Each Block)

In the hardware component of FIG. 2, the first computing unit 201 and the second computing unit 203 executes various programs stored in the storage unit 205 (such as the ROM). By this execution, following functions are realized.

(The Data Input Unit)

The data input unit 101 inputs reflected wave information of an ultrasonic as time series data. The reflected wave information is IQ data or internal data (For example, B mode data, or color Doppler data) calculated from the IQ data. One slice of data is input as a frame in time series. The reflected wave information is obtained from the external input unit 207 connected to a probe (not shown in Fig.). As a dimension of the IQ data, if points on a circle of the ultrasonic are partially scanned, the dimension is two. If points on a sphere of the ultrasonic are scanned, the dimension is three. A dimension of the internal data depends on a method for calculating the internal data. For example, if B mode data or the color Doppler data is calculated using scan information of all points of IQ data, a dimension thereof is equal to the dimension of IQ data.

(The Lossy Processing Unit)

The lossy processing unit 102 obtains first compressed data by applying lossy processing (as a first step of compression processing) to the reflected wave information (input to the data input unit 101). As to the lossy processing, first, an input signal is predicted (intra frame prediction, and/or inter frame prediction) from known information, and predictable information from the input signal. Next, by using an orthogonal transform (For example, DCT: Discrete Cosine Transform) or a wavelet transform, each block of the input signal is transformed to transform coefficients having much bias. Then, the transform coefficients are quantized to reduce information thereof.

In the case that reflected wave information (input to the data input unit 101) is two-dimension, concrete lossy processing is explained. First, the two-dimensional reflected wave information is divided into each block having a predetermined size (For example, 8×8). As to a block having a size smaller than 8×8, the loss part is supplemented (For example, an averaged value of data value in this block is assigned). As to the input signal x(n) of N points (In this example, "N=8" along vertical and horizontal directions), in order to obtain DCK coefficients y(k) by one-dimensional DCT, following equation (1) is calculated as "$C_k=1$ (k≠0) and $C_0=1/\sqrt{2}$".

$$y(k) = C_k \sum_{k=0}^{N-1} x(n)\cos\frac{(2n+1)k}{2N}\pi \quad (1)$$

The equation (1) does not include a scaling of a constant to regard the transform as the orthogonal transform (The scaling for the orthogonal transform is performed with a quantization (explained next) as a set). Next, as to DCT coefficients of two-dimensional block, quantization is executed by a quantization matrix (having a value for each position in the block) specially prepared. After DCT coefficients quantized are obtained for all blocks, they are output as the first compressed data. Moreover, in the case that the reflected wave information is three-dimension, the reflected wave information is divided into each block having a size, for example, 4×4×4, 8×8×4, or 8×8×8. By applying the orthogonal transform and quantization to each block, quantization coefficients are obtained.

Above-mentioned orthogonal transform and quantization are independent processing for each block. Accordingly, by using the second computing unit 203 to compute in M-parallel, these processing can be quickly executed.

(The Buffer)

The buffer 103 stores the first compressed data obtained by the lossy processing unit 102. Concretely, by using a ring buffer, the first compressed data (output from the lossy processing unit 102) is stored for each frame. In this case, the ring buffer can store the latest K frames. If the number of frames stored is larger than K, the ring buffer abandons the frames in order from the oldest frame. The ring buffer can be realized by the first memory 202 or the second memory 204.

(The Region Indication Unit 104)

The region indication unit 104 indicates a preserve region of the first compressed data (stored in the buffer 103) for each frame. Concretely, an indication of a preserve region is obtained from the user via the operation unit 206, and a frame corresponding to the preserve region is specified in the buffer 103. The buffer 103 outputs the frame (as the preserve region indicated by the region indication unit 104) to the lossless processing unit 105. Moreover, the region indication unit 104 can indicate all frames stored in the buffer, as the preserve region.

(The Lossless Processing Unit)

The lossless processing unit 105 obtains second compressed data by applying lossless processing (as a second step of compression processing) to the first compressed data of the preserve region indicated by the region indication unit 104. As to the lossless processing, entropy coding (For example, a variable-length coding or an arithmetic coding) is applied to coefficients quantized by the lossy processing unit 102. Concretely, as to each block, direct current (DC) coefficients in DCT coefficients quantized are output as "an output bit-length" and "coefficient data corresponding to the output bit-length" by variable-length coding. Next, by scanning coefficients except for DC in zigzag order, the number of coefficients (zero) is counted. These coefficients are output as "the number of zero and an output bit-length of coefficients (non-zero)" and "coefficient data corresponding to the output bit-length of coefficients (non-zero)" by variable-length coding. In this case, as to "the output bit-length" of DC coefficients and "the number of zero and the output bit-length of coefficients (non-zero)" of coefficients except for DC, they are output by Huffman coding. As to another data, data having an indicated bit-length is output as it is.

(The Data Output Unit 106)

The data output unit 106 outputs the second compressed data (obtained by the lossless processing unit 105) to the external storage 208, and preserves it into the external storage 208.

(The Restore Processing Unit)

The restore processing unit 107 obtains restored data by applying restore processing (of the lossy processing unit) to the first compressed data (processed by the lossy processing unit 102). Concretely, as to each transform coefficient quantized, a transform coefficient is restored by an inverse quantization to multiply a corresponding value of a quantized matrix. Then, an inverse transform (of the orthogonal transform) is applied to the transform coefficient restored. For example, in the case that DCT is used as an original transform, the inverse transform thereof is an IDCT (Inverse DCT) represented as an equation (2).

$$x(n) = \sum_{k=0}^{N-1} C_k y(k) \cos \frac{(2n+1)k}{2N} \pi \quad (2)$$

In the equation (2), a meaning of each sign is same as that in the equation (1). This equation does not include a constant scaling term necessary for IDCT to be the orthogonal transform. However, in the same way as DCT, the scaling can be performed with the inverse quantization as a set.

(The Scan Transform Unit)

The scan transform unit 108 obtains a scan transformed image by applying a geometric transform to the restored data (obtained by the restore processing unit 107. In the present embodiment, IQ data or internal data is visualized as image data. In the case of IQ data, first, the internal data for display is generated. In the case that the internal data is three-dimensional data, two-dimensionalization to extract a specific section from the internal data is executed. In the case that the internal data is two-dimensional data, for example, mapping to a fan-shape or mapping to a two-dimensional rectangle is executed to the internal data. These transforms to display the restored data is called "a scan transform".

(The Display Unit)

The display unit 109 displays the scan transformed image obtained by the scan transform unit 108. Concretely, the scan transformed image is displayed in real time via a display (not shown in Fig.) of the video display unit 210.

(Flow Chart)

As to the data processing apparatus (having above-mentioned component) according to the present embodiment, operation thereof is explained. In the data processing apparatus, lossy processing is applied to the reflected wave information in real time, and first compressed data is obtained. Continually, restore processing (of the lossy processing) and a geometric transform (for visualization) are applied to the first compressed data in real time, and image data of an inspection target is obtained. The image data is presented to a user. Then, when the user indicates at least one part of the image data as a preserve region, lossless processing is executed to the first compressed data corresponding to the preserve region, and second compressed data is obtained. The second compressed data is output to the external storage.

Figure 3:
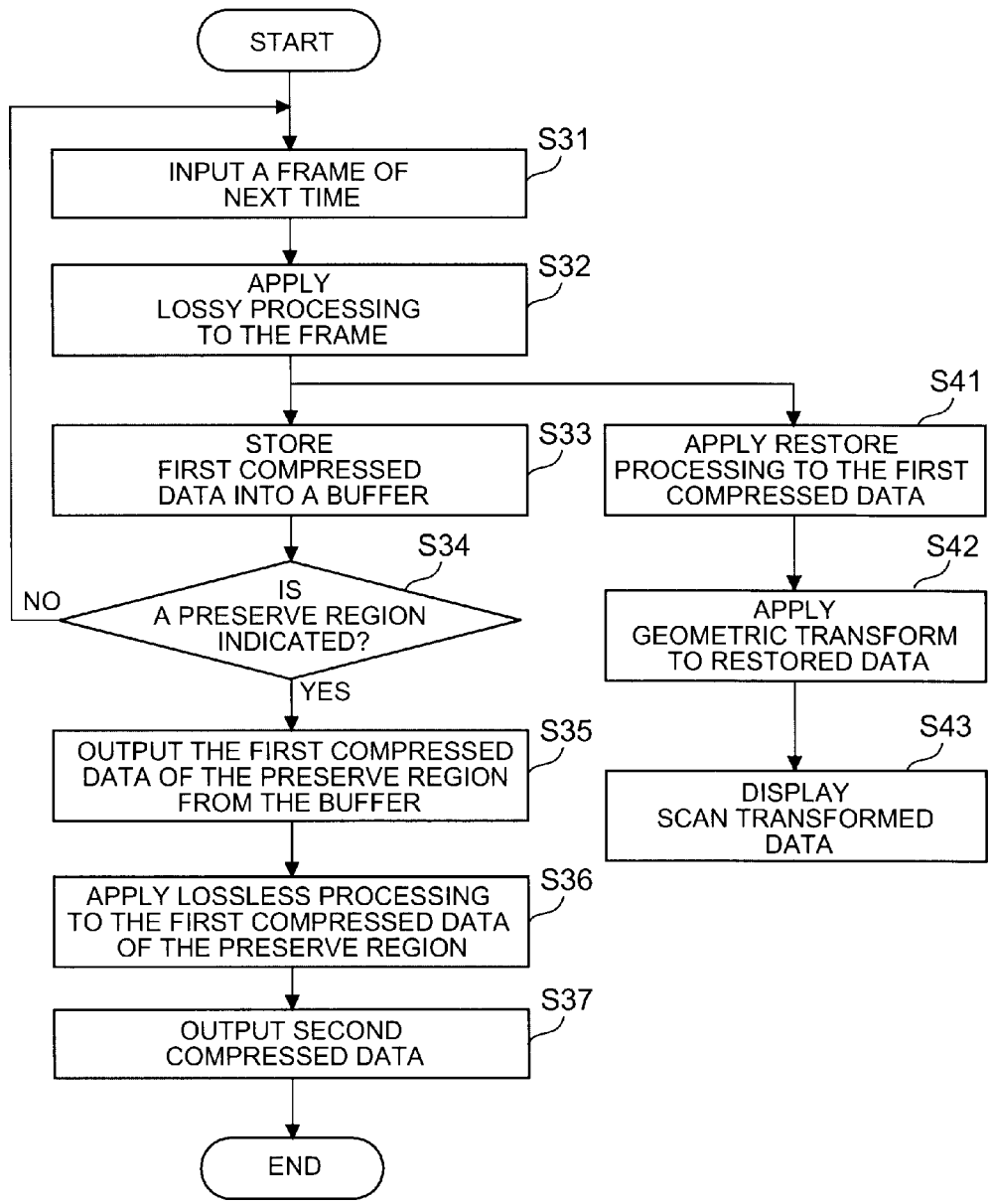
FIG. 3 is a flow chart of processing of the data processing apparatus.

FIG. 3 is a flow chart of the data processing apparatus according to the present embodiment. First, the data input unit 101 inputs the reflected wave information of each frame (S31). Next, the lossy processing unit 102 obtains first compressed data by applying lossy processing (as a first step of compression processing) to the reflected wave information (input to the data input unit 101) (S32). The lossy processing is independent for each block. Accordingly, the lossy processing is executed in M-parallel by the second computing unit 203. Next, the first compressed data (obtained by the lossy processing unit 102) is stored into the buffer 103 (S33). For example, the buffer 103 is packaged as a ring buffer. When data having a size larger than a storable size of the buffer 103 is input, the buffer 103 abandons old data from stored data thereof, and stores new data only. In parallel with this processing, the restore processing unit 107 obtains restored data by applying an inverse transform of the lossy processing to the first compressed data (S41). Continually, the scan transform unit 108 obtains a scan transformed image by applying a geometric transform to the restored data (S42). Then, the display unit 109 displays the scan transformed image on the video display unit 210 (S43).

By confirming the scan transformed image displayed by above-mentioned processing, a user indicates a preserve region to the data processing apparatus. Concretely, the operation unit 206 prepares a button to temporally stop an input of the reflected wave information (a temporal stop button), a dial to select a frame by rotating, a button to indicate the preserve region (a preserve region indication button), and a button to cancel an indication of the preserve region (a preserve region indication-cancel button). At timing when the temporal stop button is input by the user, the latest frame stored in the ring buffer is set to a notice frame, and the notice frame is switched in the ring buffer by the user's dial operation. Whenever the notice frame is switched, the notice frame is scanned, and image data thereof is displayed. A notice frame at timing when the preserve region indication button is pushed one time is set to a start frame of the preserve region. A notice frame at timing when the preserve region indication button is pushed more one time is set to an end frame of the preserve region. At timing when the preserve region indication button is pushed second time (more one time), it is decided that the user indicates the preserve region. The preserve region indication-cancel button is used for cancelling the user's indication of the preserve region immediately before pushing the preserve region indication-cancel button.

The data information apparatus decides whether the user indicates a preserve region (S34). If the preserve region is not indicated, processing is returned to S31, and a next frame is input. If the preserve region is input, the region indication unit 104 specifies a preserve region of the first compressed data stored in the buffer 103, and outputs the first compressed data corresponding to the preserve region to the lossless processing unit 105 (S35). The lossless processing unit 105 obtains second compressed data by applying lossless processing (as a second step of compression processing) to the first compressed data output from the buffer 103 (S36). Last, the data output unit 106 outputs the second compressed data to the external storage 208 (S37).

(Effect)

In this way, as to the data processing apparatus according to the present embodiment, two step processing (lossy processing, lossless processing) is applied to compress the reflected wave information. Especially, the second step processing (lossless processing) is applied to only preserve region data indicated by the user. As a result, in the data processing apparatus, a data quantity as a target of lossless processing can be reduced, and time required for compression processing can shorten.

Furthermore, as to the data processing apparatus according to the present embodiment, by applying the restore processing and the geometric transform (for visualization) to the first compressed data (obtained by the lossy transform), image data of an inspection target is presented to a user in real time. The second compressed data is generated by applying lossless processing to the first compressed data. The lossless processing assures that the second compressed data is completely restored as the first compressed data. As a result, the data processing apparatus assures that image data restored from the second compressed data is same as the image data displayed to the user in real time.

Furthermore, as to the data processing apparatus according to the present embodiment, the lossy processing (as the first step of compression processing) is executed by the computing unit able to compute in M-parallel. As a result, the data processing apparatus can quickly execute the lossy processing as the first step of regular computing.

(Modification)

In the flow chart of FIG. 3, when the preserve region is indicated at S34, processing of S31~S33 and S41~S43 may be executed in parallel. Alternatively, after stopping these steps temporally, processing of S35~S37 may be executed. Furthermore, at S36, for example, lossless processing may be executed using correlation among frames of the first compressed data. In this case, by executing the lossless processing for each frame in order, the result may be output. Alternatively, by applying the lossless processing to a lossy processing result of a plurality of frames collectively, the result may be output.

Furthermore, if the correlation among frames is used at S31~33 (For example, inter frame prediction is used), the buffer 103 stores information (For example, one bit-flag) representing whether the prediction is used for each frame. When the preserve region is specified, any of following methods (A) and (B) is utilized. As a result, a frame compressed using the correlation among frames can be correctly restored.

(A) A preserve region is adjusted so that a frame not using the prediction is located at a head position of the preserve region.

(B) If a frame using the prediction is located at the head position, a preserve region is adjusted so that another frame (located before and nearest to the frame) not using the prediction is located at the head position.

In the disclosed embodiments, the processing can be performed by a computer program stored in a computer-readable medium.

In the embodiments, the computer readable medium may be, for example, a magnetic disk, a flexible disk, a hard disk, an optical disk (e.g., CD-ROM, CD-R, DVD), an optical magnetic disk (e.g., MD). However, any computer readable medium, which is configured to store a computer program for causing a computer to perform the processing described above, may be used.

Furthermore, based on an indication of the program installed from the memory device to the computer, OS (operation system) operating on the computer, or MW (middle ware software), such as database management software or network, may execute one part of each processing to realize the embodiments.

Furthermore, the memory device is not limited to a device independent from the computer. By downloading a program transmitted through a LAN or the Internet, a memory device in which the program is stored is included. Furthermore, the memory device is not limited to one. In the case that the processing of the embodiments is executed by a plurality of memory devices, a plurality of memory devices may be included in the memory device.

A computer may execute each processing stage of the embodiments according to the program stored in the memory device. The computer may be one apparatus such as a personal computer or a system in which a plurality of processing apparatuses are connected through a network. Furthermore, the computer is not limited to a personal computer. Those skilled in the art will appreciate that a computer includes a processing unit in information processor, a microcomputer, and so on. In short, the equipment and the apparatus that can execute the functions in embodiments using the program are generally called the computer.

While certain embodiments have been described, these embodiments have been presented by way of examples only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An apparatus for processing data, comprising:
a data input unit configured to input time series data;
a lossy processing unit configured to obtain first compressed data by applying lossy processing to the time series data;
a buffer configured to store the first compressed data;
a region indication unit configured to indicate at least one part of the first compressed data;
a lossless processing unit configured to obtain second compressed data by applying lossless processing to the at least one part of the first compressed data; and
a data output unit configured to output the second compressed data.

2. The apparatus according to claim 1, further comprising:
a restore processing unit configured to obtain restored data by applying restore processing of the lossy processing to the first compressed data;
a scan transform unit configured to obtain a scan transformed image by applying a geometric transform to the restored data; and
a display unit configured to display the scan transformed image.

3. The apparatus according to claim 1, wherein
the time series data is reflected wave information of a ultrasonic.

4. The apparatus according to claim 3, wherein
the reflected wave information is any of identical phase component data (I data), orthogonal phase component data (Q data), B mode data, and color Doppler data.

5. The apparatus according to claim 1, wherein
the lossy processing includes an orthogonal transform of each block of the time series data, and a quantization of coefficients obtained by the orthogonal transform, and
the lossless processing includes a variable-length coding of the coefficients quantized by the quantization.

6. The apparatus according to claim 1, wherein
the lossy processing unit executes the lossy processing in parallel by using a computing device able to compute in M-parallel (M: a natural number larger than or equal to two).

7. A method for processing data, comprising:
inputting, by a data input unit, time series data;
obtaining, by a lossy processing unit, first compressed data by applying lossy processing to the time series data;
storing, into a buffer, the first compressed data;
indicating, by a region indication unit, at least one part of the first compressed data;
obtaining, by a lossless processing unit, second compressed data by applying lossless processing to the at least one part of the first compressed data; and
outputting, by a data output unit, the second compressed data.

8. A non-transitory computer readable medium including computer executable instructions for causing a computer to perform a method for processing data, the method comprising:
inputting time series data;
obtaining first compressed data by applying lossy processing to the time series data;
storing the first compressed data into a buffer;
indicating at least one part of the first compressed data;
obtaining second compressed data by applying lossless processing to the at least one part of the first compressed data; and
outputting the second compressed data.

* * * * *